(12) United States Patent
Stadler et al.

(10) Patent No.: US 6,528,246 B2
(45) Date of Patent: *Mar. 4, 2003

(54) METHOD FOR THE INACTIVATION OF NON-LIPID-COATED VIRUSES

(75) Inventors: Monika Stadler, Schwechat (AT); Horst Schwinn, Marburg (DE); Djuro Josic, Vienna (AT); Werner Gehringer, Vienna (AT); Frederic Bal, Vienna (AT)

(73) Assignee: Octapharma AG, Ziegelbrucke (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/501,034

(22) PCT Filed: Feb. 5, 1995

(86) PCT No.: PCT/EP94/00328
§ 371 (c)(1),
(2), (4) Date: Sep. 28, 1995

(87) PCT Pub. No.: WO94/17834
PCT Pub. Date: Aug. 18, 1994

(65) Prior Publication Data
US 2002/0068355 A1 Jun. 6, 2002

(30) Foreign Application Priority Data
Feb. 9, 1993 (DE) .......... 43 03 609
Jun. 3, 1993 (DE) .......... 43 18 435

(51) Int. Cl.[7] .......... A01N 1/02; C12N 7/04; C12N 7/06
(52) U.S. Cl. .......... 435/2; 435/236; 435/238
(58) Field of Search .......... 435/2, 238, 236

(56) References Cited

U.S. PATENT DOCUMENTS 4,540,573 A * 9/1985 Neurata et al. .......... 424/85
5,118,795 A 6/1992 Rubinstein .......... 530/383
5,151,499 A * 9/1992 Kameyama et al. .......... 530/381

FOREIGN PATENT DOCUMENTS

| EP | 0131740 | 1/1985 |
| EP | 0306778 | 3/1989 |
| EP | 0367840 | 5/1990 |
| EP | 0378208 | 7/1990 |
| EP | 0479597 | 4/1992 |
| EP | 0519901 A2 | 12/1992 |

OTHER PUBLICATIONS

Virological Safety Aspects of Plasma Derivatives, Cannes, France (Nov. 3–Nov. 6, 1992) Fred Brown.
T. Nowak et al. Inactivation of HIV, HBV, HCV Related Viruses . . . Dev. Biol. Stand. 1993, vol. 81, pp. 169–176.
Derwent Publications, Ltd., JPA 2 180 833 (Green Cross) Jul. 13, 1990 (Section Ch Week 9034).
Journal of Med. Vir. 41:61–64 (1993); Inactivation of Hepatitis A Virus by Heat Treatment in Aqueous Solution.
Siegl et al., "Stability of Hepatitis A Virus", Intervirology 22: 218–226 (1984).*
Lelie et al., "Inactivation of 12 Viruses by Heating Steps Applied during Manufacture of Hepatitis B Vaccine", J. Med. Virol. 23(3): 297–302 (1987).*
Translation of JP 2–180833 Previously Cited.*
Burnouf–Radosevich, et al., "A Pasteurized Therapeutic Plasma," *Infusionstherapie* (1992) pp. 91–94.
Horowitz, et al., "Inactivities of viruses in labile blood derivatives," *Transfusion* 25 (1985) 523–527.

* cited by examiner

Primary Examiner—Christopher R. Tate
(74) Attorney, Agent, or Firm—Jacobson Holman PLLC

(57) ABSTRACT

A method for the inactivation of viruses, in particular those having no lipid coats, in protein-containing compositions from blood, blood plasma or similar natural sources by treating said source, simultaneously or succesively, with an effective amount of dialkyl or trialkyl phosphates and optionally surfactants at an elevated temperature in the range of from 55° C. to 67° C. for five hours to 30 hours.

20 Claims, No Drawings

METHOD FOR THE INACTIVATION OF NON-LIPID-COATED VIRUSES

The object of the present application is a method for the inactivation of non-lipid-coated viruses in protein-containing compositions from blood, blood plasma or similar natural sources.

EP 0 131 740 B1 describes a method for the inactivation of viruses in compositions containing labile proteins. The viruses to be inactivated contain lipids and in particular may have a lipid coat. The composition to be freed from lipid-containing viruses is derived from a natural source selected from the group consisting of whole blood, blood plasma, plasma concentrate, precipitate from any fractioning of such plasma, supernatant from any fractioning of such plasma, serum, cryoprecipitate, cell lysate, proteins induced in blood cells, product of a normal or cancer cell which is not derived from blood, and product of a gene splicing process. The method described in EP 0 131 740 B1 consists in contacting the composition containing labile protein with an effective amount of a dialkyl or trialkyl phosphate for a period of time sufficient to render the composition containing labile protein free of lipid-containing viruses without causing substantial denaturing of proteins. The method described for the inactivation of lipid-containing viruses may be combined with heat treatment at 50 to 70° C. for at least 5 hours.

In preparations of the type mentioned above, however, it is increasingly important to inactivate those viruses as well that do not contain any lipid, in particular those which have no lipid coat ("non-lipid-coated viruses"). The group of non-lipid-coated viruses, which are to be considered "viruses containing no lipid" in the sense of EP 0 131 740 B1, include, in particular, hepatitis A viruses, parvoviruses, such as parvovirus B 19, and polioviruses. Such viruses may be present as pathogens in blood, plasma, serum, cryoprecipitate, cell lysate and similar natural sources.

It is an object of the present invention to provide a method allowing to inactivate viruses which contain no lipid coat or only a few lipids and are present in certain preparations. Such preparations may include, in particular, compositions containing labile proteins from whole blood, blood plasma, plasma concentrate, precipitate from any fraction of such plasma, supernatant from any fractioning of such plasma, serum, cryoprecipitate, cell lysate, or similar natural sources.

Surprisingly, this object is achieved by a method which inactivates viruses, in particular those which have no lipid coats, in compositions containing protein from blood, blood plasma or similar natural sources by treating said source, simultaneously or succesively, with an effective amount of dialkyl or trialkyl phosphates and optionally surfactants at an elevated temperature in the range of from 55°C. to 67° C. for 5 to 30 hours.

The amount of dialkyl or trialkyl phosphate preferably ranges between 0.001% and 1%. For carrying out this method, the temperature is preferably adjusted at from 60° C. to 65° C. The duration of the heat treatment preferably is at least 10 hours.

The protein fraction in which the viruses containing no lipids are to be inactivated is derived, in particular, from natural sources of the type mentioned above and, in particular, may have been enriched with the corresponding protein by precipitation or chromatographic methods prior to the inactivation reaction.

Enrichment of the protein fraction using chromatographic methods, as described in EP 0 367 840 A1, has proven to be particularly useful. This involves first subjecting the natural source providing the protein to anion-exchange chromatography. Chromatographic substrate materials modified with diethylaminoethylene groups have proven to be particularly useful.

Then, the natural source or the fraction enriched from the natural source is subjected to the above-described virus inactivation method by heat treatment and treatment with dialkyl or trialkyl phosphates.

It has been found advantageous to perform said treatment with dialkyl or trialkyl phosphates in the presence of surfactants. As alkyl phosphates, there may be used, in particular, the phosphates mentioned in EP 0 131 740 B1, such as dialkyl phosphates or trialkyl phosphates having alkyl groups containing from 1 to 10 carbon atoms, especially from 2 to 10 carbon atoms. In particular, trialkyl phosphates, such as tri-n-butyl phosphate, tri-t-butyl phosphate, tri-n-hexyl phosphate, tri(2-ethylhexyl) phosphate, and tri-n-decyl phosphate, may be used. Mixed trialkyl phosphates are also useful. Similarly, the correspondingly substituted dialkyl phosphates or mixtures of such dialkyl or trialkyl phosphates may also be employed.

As surfactants, there may be used, in particular, non-toxic detergents. As non-ionic detergents, which should be present in amounts of at least 0.1% by weight, the following derivatives may be mentioned: polyoxyethylene derivatives of fatty acids, partial esters of sorbitol anhydride, e.g. products known by the trade names of Tween 80, Tween 20, and Polysorbat 80, as well as oil-soluble non-ionic surfactants, in particular those known by the trade name of Triton X100 (ethoxylated alkyl phenols). Zwitterionic reagents, for instance sulfobetains, such as N-dodecyl-N,N-dimethyl-2-ammonio-1-ethanesulfonate or derivatives thereof, or non-ionic detergents, such as octyl-β-D-glucopyranosides, may also be used. The amount of surfactant is preferably from 0.01% to 10%.

Especially preferred are combinations of tri-n-butyl phosphate and Tween, or sodium cholate/TNBP (tri-n-butyl phosphate).

It has been found to be advantageous to perform this treatment at elevated temperatures in the presence of auxiliary agents, such as saccharose, sorbitol, or short-chain neutral amino acids. In principle, the stabilizing factors mentioned in EP 0 018 561 and/or DE 40 01 451 A1 may be used in the stated amounts. The concentration of the auxiliary substances (stabilizing factors) may be very high, for instance, the saccharose concentration is preferred to be up to 200% by weight. As short-chain amino acids, glycine, lysine and/or arginine, in particular, may be used.

Surprisingly, it has been shown that the treatment of the protein-containing compositions from blood, blood plasma or similar natural sources may be performed even without an addition of calcium ions at elevated temperatures. In EP 0 106 269, the addition of calcium ions is considered to be necessarily required. Thus, EP 0 106 269 discloses that $Ca^{2+}$ stabilizes fractions of antihemophilic cryoprecipitate in the pasteurizing process described therein. This is not necessary according to the invention.

The treatment with dialkyl or trialkyl phosphates, optionally at elevated temperatures, may be followed by a chromatographic purification step. This chromatographic purification step is preferably performed on anion-exchange materials, such as DEAE modified ion-exchange resins. The pH value should be in the range of from 6 to 8.5.

The pharmacologically significant proteins thus enriched or obtained, such as factor VIII, factor IX, fibrinogen, gamma-globulin etc., contain no active viruses of the types hepatitis A, parvoviruses, such as parvovirus B 19, or polioviruses.

The method according to the invention will be illustrated in more detail by the following example for the inactivation of lipid-free viruses in a factor VIII preparation.

EXAMPLE 1

Commercial cryoprecipitate is applied on a column filled with Fractogel® DEAE resin. The effluate is collected and examined for factor VIII activity. Then, the column is washed with a buffer containing 110 mM sodium chloride, 10 mM sodium citrate×5 H$_2$O, 120 mM glycine, 1 mM calcium chloride×2 H$_2$O, pH 6.9 to 7.0 (to be adjusted with 1 M HCl). Subsequently, the column is treated with a buffer having the following composition: 250 mM sodium chloride, 20 mM sodium citrate×5H$_2$O, 80 mM glycine, 16 mM Lysine, 2.5 mM calcium chloride×2 H$_2$O, pH 6.9 to 7.0.

To the fraction thus obtained, saccharose is added. Then, the fraction is kept at 64° C. for 12 hours with addition of tri-nbutyl phosphate/Tween (0.1%/0.3%). Then, ion-exchange chromatography is again performed on TSK Fractogel® DEAE or EMD Fractogel® DEAE.

The factor-VIII active fraction is eluted with a buffer containing 250 mM sodium chloride, 20 mM sodium citrate×5 H$_2$O, 80 mM glycine, 16 mM Lysine, 2.5 mM calcium chloride×2 H$_2$O.

EXAMPLE 2

Virus inactivation is performed without the presence of calcium ions by treating the commercial cryoprecipitate as described in Example 1 with no calcium compounds being added to the buffers (washing buffer and elution buffer) prior to the heat treatment. Then, heat treatment is performed without addition of calcium ions and further processing is as described in Example 1.

What is claimed is:

1. A method for inactivating hepatitis A virus, parvovirus, or poliovirus in a protein-containing composition from a natural source comprising the steps of
   a) adding to the composition a stabilizer selected from the group consisting of saccharose, sorbitol, and a short-chain neutral amino acid, wherein the composition is blood or a preparation obtained from blood, and wherein the protein is pharmacologically active blood protein, followed by,
   b) treatment of the composition by (i) adding to the composition an effective amount of a dialkyl or trialkyl phosphate and (ii) heating the composition at a temperature of over 60° C. up to 65° C. for a time of 5–30 hours in the presence of the phosphate;
whereby, essentially no active hepatitis A virus, parvovirus, or poliovirus remains in the protein-containing composition and the blood protein remains pharmacologically active.

2. The method according to claim 1 wherein the amount of the dialkyl or trialkyl phosphate is 0.001–1% by weight of the composition.

3. The method according to claim 1 wherein heating is for a time of at least 10 hours.

4. The method according to claim 1 further comprising the step of, preceding the treatment step, enriching the protein-containing composition by a chromatographic or precipitation method.

5. The method according to claim 1 further comprising the step of, preceding the treatment step, adding to the composition an auxiliary substance selected from the group consisting of saccharose, sorbitol, and short-chain neutral amino acids.

6. The method according to claim 5 wherein the auxiliary substance is saccharose, the amount of which is a maximum of 200% by weight of the composition.

7. The method according to claim 5 wherein the auxiliary substance is an amino acid selected from the group consisting of glycine, lysine, arginine, and a combination thereof.

8. The method according to claim 1 performed in the absence of any added calcium ions.

9. The method according to claim 1 further comprising, following the treatment step, the step of subjecting the composition to chromatographic purification.

10. The method according to claim 1 wherein the pH of the composition is maintained at 6.0 to 8.5.

11. The method according to claim 1 wherein the treatment step involves the dialkyl or trialkyl phosphate and a surfactant.

12. The method according to claim 11 wherein the amount of the dialkyl or trialkyl phosphate is between 0.001%–1% by weight of the composition.

13. The method according to claim 11 wherein heating is for a time of at least 10 hours.

14. The method according to claim 11 further comprising the step of, preceding the treatment step, enriching the protein-containing composition by a chromatographic or precipitation method.

15. The method according to claim 11 further comprising the step of, preceding the treatment step, adding to the composition an auxiliary substance selected from the group consisting of saccharose, sorbitol, and short-chain neutral amino acids.

16. The method according to claim 15 wherein the auxiliary substance is saccharose at a maximum amount of 200% by weight of the composition.

17. The method according to claim 15 wherein the auxiliary substance is an amino acid selected from the group consisting of glycine, lysine, arginine, and a combination thereof.

18. The method according to claim 11 performed in the absence in the absence of any added calcium ions.

19. The method according to claim 11 further comprising, following the treatment step, the step of subjecting the composition to chromatographic purification.

20. The method according to claim 11 wherein the pH of the composition is maintained at 6.0 to 8.5.

* * * * *